United States Patent
Lei et al.

(10) Patent No.: US 9,777,244 B2
(45) Date of Patent: Oct. 3, 2017

(54) HYDROGEL FRAGRANCE CAPSULE, FORMULATIONS AND PROCESS FOR PREPARING THE SAME

(71) Applicant: International Flavors & Fragrances Inc., New York, NY (US)

(72) Inventors: Yabin Lei, Holmdel, NJ (US); Xihua Lu, Holmdel, NJ (US); Carol Joyce, Toms River, NJ (US); Li Xu, Newark, NJ (US)

(73) Assignee: INTERNATIONAL FLAVORS & FRAGRANCES INC., New York, NY (US)

( * ) Notice: Subject to any disclaimer, the term of this patent is extended or adjusted under 35 U.S.C. 154(b) by 0 days.

(21) Appl. No.: 14/414,376

(22) PCT Filed: Jul. 11, 2013

(86) PCT No.: PCT/US2013/050054
§ 371 (c)(1),
(2) Date: Jan. 12, 2015

(87) PCT Pub. No.: WO2014/011860
PCT Pub. Date: Jan. 16, 2014

(65) Prior Publication Data
US 2015/0203787 A1    Jul. 23, 2015

Related U.S. Application Data

(60) Provisional application No. 61/671,258, filed on Jul. 13, 2012.

(51) Int. Cl.
| | | |
|---|---|---|
| *C11D 3/50* | (2006.01) | |
| *A61K 8/81* | (2006.01) | |
| *A61K 8/11* | (2006.01) | |
| *A61Q 15/00* | (2006.01) | |
| *A61Q 5/02* | (2006.01) | |
| *C11B 9/00* | (2006.01) | |
| *A61Q 13/00* | (2006.01) | |
| *A61K 8/73* | (2006.01) | |
| *A61Q 19/10* | (2006.01) | |
| *A61K 8/02* | (2006.01) | |
| *A61Q 5/12* | (2006.01) | |

(52) U.S. Cl.
CPC .............. *C11B 9/00* (2013.01); *A61K 8/0241* (2013.01); *A61K 8/11* (2013.01); *A61K 8/731* (2013.01); *A61K 8/8147* (2013.01); *A61K 8/8152* (2013.01); *A61Q 5/02* (2013.01); *A61Q 5/12* (2013.01); *A61Q 13/00* (2013.01); *A61Q 15/00* (2013.01); *A61Q 19/10* (2013.01); *C11D 3/505* (2013.01); *A61K 2800/10* (2013.01); *A61K 2800/412* (2013.01); *A61K 2800/56* (2013.01); *A61K 2800/614* (2013.01)

(58) Field of Classification Search
None
See application file for complete search history.

(56) References Cited

U.S. PATENT DOCUMENTS

| | | | | |
|---|---|---|---|---|
| 7,833,960 B2 * | 11/2010 | Lei | ............................. | A61K 8/11 510/441 |
| 9,233,353 B2 * | 1/2016 | Laubender | ............... | B01J 13/14 |
| 2005/0227907 A1 * | 10/2005 | Lee | .......................... | A61K 8/11 512/4 |
| 2011/0223314 A1 | 9/2011 | Zhang et al. | | |

FOREIGN PATENT DOCUMENTS

| | | |
|---|---|---|
| JP | 2012011269 A | 1/2012 |
| WO | 2010119020 A1 | 10/2010 |
| WO | WO2012/075293 A2 | 6/2012 |

OTHER PUBLICATIONS

IPRP, Jan. 22, 2015, PCT/US2013/050054.
Extended European Search Report mailed Nov. 3, 2015 for EP Application No. 13817113.7.
Chinese First Office Action issued Jul. 2016 for Application No. CN 2013800373861 (with English Translation included).

* cited by examiner

*Primary Examiner* — Abigail Fisher
(74) *Attorney, Agent, or Firm* — Martin Zhang; XuFan Tseng; Elizabeth M. Stover

(57) ABSTRACT

This invention is a hydrogel capsule with a fragrance or odorant encapsulated therein during the polymerization process. The hydrogel capsule is of use in fabric care or personal care formulations.

27 Claims, 3 Drawing Sheets

HYDROGEL FRAGRANCE CAPSULE, FORMULATIONS AND PROCESS FOR PREPARING THE SAME

CROSS REFERENCE TO RELATED APPLICATIONS

This application is the national stage entry under 35 USC 371 for PCT/US2013/050054, filed on Jul. 11, 2013, which claims the benefit of U.S. Provisional Application No. 61/671,258 filed on Jul. 13, 2012. The contents of the foregoing applications are incorporated herein by reference.

INTRODUCTION

Background

For protection of valuable chemical compounds such as fragrances or odorants, the use of encapsulation is increasingly being considered or is already being practiced. Encapsulation refers to processes whereby an active ingredient is placed into a stabilized form in order to allow it to be conveniently stored, or protected from unfavorable conditions, until needed. The release of active ingredient from the protected form may be rapid (such as by crushing, or by ingestion), or gradual (such as by dissolution, diffusion, or bio-degradation). In this manner it is possible to maximize the effectiveness of the active ingredient by ensuring that it is released at the proper time.

The term "microcapsule" has been used to describe small particles or beads, which range in size from less than one micron, up to several millimeters, which may contain a wide variety of active ingredients (Thies (1994) *Today's Chemist* November p. 40; Goodwin (1974) *Chemtech Magazine* October p 623-626). Microcapsules can be divided into two broad groups: (1) "Aggregate" type microcapsules having the active ingredient dispersed uniformly throughout a continuous matrix. The matrix may be a solid dry polymer or a gel swollen with solvent. In the case where the gel is swollen with water, the term "hydrogel" is applied. Hydrogel encapsulation systems of this type have been described and are generally based on cross-linked forms of water-soluble polymers such as alginate, gelatin, pectin, agar, gellan, or starch (Sanderson, et al. (1989) Cereal *Foods World* 34(12): 993-998). (2) "Mononuclear" microcapsules, on the other hand, are composed of materials that show a true "shell-core" morphology. These are similar to an egg in that they have a solid shell or flexible membrane surrounding a core which may be a liquid, a solid, or even a gel.

U.S. Pat. No. 3,808,686 discloses the preparation of an organic solution of a water-insoluble, organic solvent soluble hydrophilic polymer for application to denture prostheses to eliminate denture breath. However, this preparation is strictly a matrix-based system, wherein the active ingredient is entrapped by physical absorption, which is not suitable for consumer applications such as personal care and fabric.

U.S. Pat. No. 3,660,563 discloses water-soluble polymers containing fragrances, drugs, soaps, etc. entrapped therein. However, this is a particle-based system that would not be able to retain fragrance oil in a base.

EP 1146057 discloses cross-linked polymeric nanoparticles for carrying skin care ingredients, e.g., fragrances, essential oils, etc. and food ingredients. However, this is, as claimed, a particle approach, wherein the fragrance is loaded in situ and the particle size is in the nanometer range, which would have poor stability in personal care and fabric application.

US 2002/0050659 teaches hydrocapsules for encapsulating a liquid, e.g., a solution, fluid, slurry, paste or suspension. However, the hydrocapsules of this document are coextruded and have low loading capacity and stability.

US 2012/0058929 teaches a microcapsule carrier system for fragrances, wherein the core of the microcapsule is composed of a fragrance or odorant and the shell is obtained by polymerizing one or more C1-C24 alkyl esters of acrylic acid and/or methacrylic acid; and methyl methacrylate (MMA), 1,4-butanediol diacrylate (BDA), pentaerthrityl triacrylate (PETIA) and/or ethylene glycol dimethacrylate (EDGMA). However, the microcapsules of this reference are small, have poor stability, and have a high level of polymer wall material compared to core material.

SUMMARY OF THE INVENTION

This invention is a hydrogel capsule, a consumer product (e.g., a laundry care, personal care, therapeutic, cosmetic or cosmeceutic product) containing the hydrogel capsule and a method for preparing the hydrogel capsule. The hydrogel capsule of the invention is composed of a fragrance or odorant encapsulated in at least one polymerized acrylic or methacrylic acid, or ester thereof, wherein the hydrogel capsule has a mean diameter in the range of 1 to 100 µm, preferably from 1 to 20 µm and the fragrance or odorant is encapsulated in the hydrogel capsule during polymerization of the acrylic or methacrylic acid, or ester thereof. In some embodiments, the polymerizable acrylic or methacrylic acid, or ester thereof, is a multifunctional acrylate or methacrylate, e.g., ethylene glycol dimethacrylate, poly(ethylene glycol) dimethacrylate, poly(ethylene glycol) diacrylate, or 1,6-hexandiol dimethacrylate, and is polymerized alone or copolymerized with a monofunctional methacrylate or acrylate to form the shell of the capsule.

The method of producing the hydrogel capsule involves the steps of (a) providing a aqueous phase comprising an emulsifier; (b) providing an oil phase comprising at least one acrylic or methacrylic acid, or ester thereof, and a fragrance or odorant; (c) emulsifying the aqueous phase of (a) with the oil phase of (b) to produce an emulsion; (d) polymerizing the emulsion to produce a hydrogel capsule with a fragrance or odorant encapsulated therein; (e) curing the hydrogel capsule at room temperature; and (f) curing the hydrogel capsule, e.g., at elevated temperature of at least 40° C., or more preferably in the range of 55 to 95° C., or 55 to 65° C.

Laundry care, personal care, therapeutic, cosmetic or cosmetic products containing the hydrogel capsule of this invention are also provided.

DETAILED DESCRIPTION OF THE INVENTION

Figure 1:
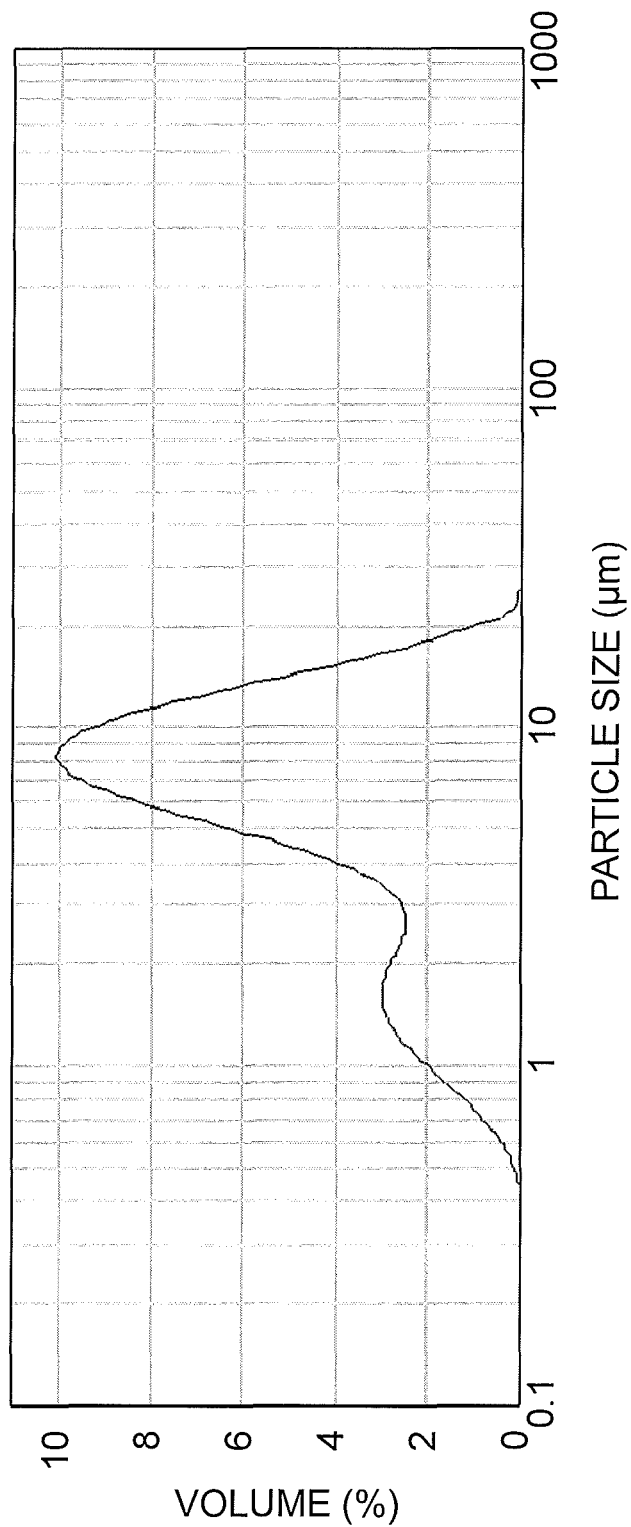
FIG. 1 shows the particle size distribution of hydrogel capsules of this invention.

This invention relates to a hydrogel capsule carrier for fragrances or odorants, the production thereof and the use of the carrier in providing a fragrance or odorant to a fabric care product or personal care product, e.g., hair conditioner/shampoo, body lotion, or hair refresher, as well as washing or cleaning compositions for laundry and surface treatment. The hydrogel capsules of this invention are composed of a fragrance or odorant encapsulated in at least one polymerized acrylic or methacrylic acid, or ester thereof, wherein the fragrance or odorant is encapsulated in the hydrogel capsule during polymerization of the acrylic or methacrylic acid, or ester thereof. These hydrogel capsules enable the valuable active ingredient to be provided already distributed relatively homogeneously in a use mixture, without having to expose it to the other constituents during storage.

A fragrance or odorant is understood to mean all organic substances which have a desired olfactory property and are essentially nontoxic. This includes all fragrances or odorants used customarily in washing or cleaning compositions or in perfumery and includes fragrance mixtures or blends. A fragrance or odorant may be a compound of natural, semi-synthetic or synthetic origin. Preferred fragrances or odorants can be assigned to the substance classes of the hydrocarbons, aldehydes or esters. The fragrances or odorants also include natural extracts and/or essences which may include complex mixtures of constituents, such as orange oil, lemon oil, rose extract, lavender, musk, patchouli, balsam essence, sandalwood oil, pine oil and cedar oil.

Nonlimiting examples of synthetic and semisynthetic fragrances or odorants are: 7-acetyl-1,2,3,4,5,6,7,8-octahydro-1,1,6,7-tetramethylnaphthalene, α-ionone, β-ionone, γ-ionone, α-isomethylionone, methyl cedryl ketone, methyl dihydrojasmonate, methyl 1,6,10-trimethyl-2,5,9-cyclodo-decatrien-1-yl ketone, 7-acetyl-1,1,3,4,4,6-hexamethyltetralin, 4-acetyl-6-tert-butyl-1,1-dimethylindane, hydroxyphenylbutanone, benzophenone, methyl β-naphthyl ketone, 6-acetyl-1,1,2,3,3,5-hexamethylindane, 5-acetyl-3-isopropyl-1,1,2,6-tetramethylindane, 1-dodecanal, 4-(4-hydroxy-4-methylpentyl)-3-cyclohexene-1-carboxaldehyde, 7-hydroxy-3,7-dimethyloctanal, 10-undecen-1-al, isohexenylcyclohexylcarboxaldehyde, formyltricyclodecane, condensation products of hydroxycitronellal and methyl anthranilate, condensation products of hydroxycitronellal and indole, condensation products of phenylacetaldehyde and indole, 2-methyl-3-(para-tert-butylphenyl)propionaldehyde, ethylvanillin, heliotropin, hexylcinnamaldehyde, amylcinnamaldehyde, 2-methyl-2-(isopropylphenyl)propionaldehyde, coumarin, decalactone-γ, cyclopentadecanolide, 16-hydroxy-9-hexadecenolactone, 1,3,4,6,7,8-hexahydro-4,6,6,7,8,8-hexamethylcyclopenta-γ-2-benzopyran, β-naphthol methyl ether, ambroxan, dodecahydro-3a,6,6,9a-tetramethylnaphtho[2,1b]furan, cedrol, 5-(2,2,3-trimethylcyclopent-3-enyl)-3-methylpentan-2-ol, 2-ethyl-4-(2,2,3-trimethyl-3-cyclopenten-1-yl)-2-buten-1-ol, caryophyllene alcohol, tricyclodecenyl propionate, tricyclodecenyl acetate, benzyl salicylate, cedryl acetate and tert-butylcyclohexyl acetate.

Further examples of fragrances or odorants of use in this invention are described, for example, in U.S. Pat. Nos. 6,143,707; 6,703,011; and 5,089,162; EP 1 360 270 and WO 2009/027957.

Other fragrances are essential oils, resinoids and resins from a multitude of sources, such as peru balsam, olibanum resinoid, styrax, labdanum resin, nutmeg, cassia oil, benzoin resin, coriander and lavandin. Further suitable fragrances are: phenyl ethyl alcohol, terpineol, linalool, linalyl acetate, geraniol, nerol, 2-(1,1-dimethylethyl)cyclohexanol acetate, benzyl acetate and eugenol.

The fragrances provided in Table 1 are amongst those suitable for inclusion within the capsule of the present invention.

TABLE 1

| Perfume Ingredient | ClogP |
| --- | --- |
| Allyl cyclohexane propionate | 3.935 |
| Ambrettolide | 6.261 |
| Amyl benzoate | 3.417 |
| Amyl cinnamate | 3.771 |
| Amyl cinnamic aldehyde | 4.324 |
| Amyl cinnamic aldehyde dimethyl acetal | 4.033 |
| Iso-amyl salicylate | 4.601 |
| AURANTIOL (Hydroxycitronellal-methylanthranilate) | 4.216 |
| Benzyl salicylate | 4.383 |
| Para-tert-Butyl cyclohexyl acetate | 4.019 |
| Iso butyl quinoline | 4.193 |
| beta-Caryophyllene | 6.333 |
| Cadinene | 7.346 |
| Cedrol | 4.530 |
| Cedryl acetate | 5.436 |
| Cedryl formate | 5.070 |
| Cinnamyl cinnamate | 5.480 |
| Cyclohexyl salicylate | 5.265 |
| Cyclamen aldehyde | 3.680 |
| Diphenyl methane | 4.059 |
| Diphenyl oxide | 4.240 |
| Dodecalactone | 4.359 |
| ISO E SUPER (1-(1,2,3,4,5,6,7,8-Octahydro-2,3,8,8-tetramethyl-2-naphthalenyl)-ethanone) | 3.455 |
| Ethylene brassylate | 4.554 |
| Ethyl undecylenate | 4.888 |
| EXALTOLIDE (15-Hydroxyentadecanloic acid, lactone) | 5.346 |
| GALAXOLIDE (1,3,4,6,7,8-Hexahydro-4,6,6,7,8,8-hexamethylcyclopenta-gamma-2-benzopyran) | 5.482 |
| Geranyl anthranilate | 4.216 |
| Geranyl phenyl acetate | 5.233 |
| Hexadecanolide | 6.805 |
| Hexenyl salicylate | 4.716 |
| Hexyl cinnamic aldehyde | 5.473 |
| Hexyl salicylate | 5.260 |
| Alpha-Irone | 3.820 |
| LILIAL (para-tertiary-butyl-alpha-methyl hydrocinnamic aldehyde) | 3.858 |
| Linalyl benzoate | 5.233 |
| Methyl dihydrojasmone | 4.843 |
| Gamma-n-Methyl ionone | 4.309 |
| Musk indanone | 5.458 |
| Musk tibetine | 3.831 |
| Oxahexadecanolide-10 | 4.336 |
| Oxahexadecanolide-11 | 4.336 |
| Patchouli alcohol | 4.530 |
| PHANTOLIDE (5-Acetyl-1,1,2,3,3,6-hexamethyl indan) | 5.977 |
| Phenyl ethyl benzoate | 4.058 |
| Phenylethylphenylacetate | 3.767 |
| Phenyl heptanol | 3.478 |
| Alpha-Santalol | 3.800 |
| THIBETOLIDE (15-Hydroxypentadecanoic acid, lactone) | 6.246 |
| Delta-Undecalactone | 3.830 |
| Gamma-Undecalactone | 4.140 |
| Vetiveryl acetate | 4.882 |
| Ylangene | 6.268 |
| Methyl Beta Napthyl Ketone | 1.99 |
| Terpeneol Couer | 2.67 |
| Geraniol | 2.7 |
| Dihydromyrcenol | 2.99 |
| Citronellol 950 | 3.3 |
| Tetrahydromyrcenol | 3.54 |

The higher C log P materials are preferred, meaning that those materials with a C log P value of 4.5 are preferred over those fragrance materials with a C log P of 4.0; and those materials with a C log P value of 4.0 are preferred over the fragrance materials with a C log P of 3.3.

The fragrance formulation of the present invention preferably have at least about 40 weight percent of materials with C log P greater than 3.3, preferably greater than about 80 and more preferably greater than about 90 weight percent of materials with C log P greater than 4.0.

In an additional embodiment, the fragrance formulation may contain fragrance materials with a C log P greater than about 1.5.

Those with skill in the art appreciate that fragrance formulations are frequently complex mixtures of many fragrance ingredients. A perfumer commonly has several thousand fragrance chemicals to work from. Those with skill in the art appreciate that the present invention may contain a single ingredient, but it is much more likely that the present invention will include at least eight or more fragrance chemicals, more likely to contain twelve or more and often twenty or more fragrance chemicals. The present invention also contemplates the use of complex fragrance formulations containing fifty or more fragrance chemicals, seventy five or more, or even a hundred or more fragrance chemicals in a fragrance formulation.

Preferred fragrance materials will have both high C log P and high vapor pressure. Among those having these properties are: Para cymene, Caphene, Mandarinal Firm, Vivaldie, Terpinene, Verdox, Fenchyl acetate, Cyclohexyl isovalerate, Manzanate, Myrcene, Herbavert, Isobutyl isobutyrate, Tetrahydrocitral, Ocimene and Caryophyllene.

Preferably, the fragrance or odorant or the mixture of fragrances or odorants makes up at least 50% by mass, preferably 60 to 90% by mass, or more preferably 70 to 80% by mass of the oil phase used in preparing the hydrogel capsule of this invention.

In order to provide the highest fragrance impact from the fragrance encapsulated capsules deposited on the various substrates referenced herein, it is preferred that materials with a high odor-activity be used. Materials with high odor-activity can be detected by sensory receptors at low concentrations in air, thus providing high fragrance perception from low levels of deposited capsules. This property must be balanced with the volatility as described herein. Some of the principles mentioned above are disclosed in U.S. Pat. No. 5,112,688.

The polymerizable material used in the preparation of the hydrogel capsules of this invention is typically a monofunctional or multifunctional acrylic or methacrylic acid, or ester thereof. Such compounds are known and can be used in various proportions as blends or mixtures. Representative monofunctional monomers which can be employed according to this invention include but are not limited to acrylic acid, methacrylic acid, 2-hydroxyethyl acrylate, methyl acrylate, ethyl acrylate, propyl acrylate, n-butyl acrylate, pentyl acrylate, hexyl acrylate, 2-ethylhexyl acrylate, heptyl acrylate, octyl acrylate, nonyl acrylate, decyl acrylate, dodecyl acrylate, tetradecyl acrylate, hexadecyl acrylate, isopropyl acrylate, isobutyl acrylate, sec-butyl acrylate, 2-methylbutyl acrylate, 3-methylbutyl acrylate, 1-ethylpropyl acrylate, 2-methylpentyl acrylate, 2-ethylbutyl acrylate, 1,3-dimethylbutyl acrylate, 1-methylhexyl acrylate, 2-ethylhexyl acrylate, 1-methylheptyl acrylate, 4-ethyl-1-methyloctyl acrylate, 4-ethyl-1,1-isobutyloctyl acrylate, allyl acrylate, 2-methylallyl acrylate, 1-methylallyl acrylate, 2-butenyl acrylate, 1,3-dimethyl-3-dibutenyl acrylate, 3,7-dimethyl-7-octenyl acrylate, 3,7-dimethyl-2,6-octadienyl acrylate, 3,7-dimethyl-6-octenyl acrylate, tert-butyl acrylate. Representative ester monomers of methacrylic acid, which can be used include 2-hydroxyethyl methacrylate, glycidyl methacrylate, methyl methacrylate, ethyl methacrylate, n-propyl methacrylate, isopropyl methacrylate, n-butyl methacrylate, isobutyl methacrylate, sec-butyl methacrylate, tert-butyl methacrylate, n-hexyl methacrylate, n-octyl methacrylate, isooctyl methacrylate, decyl methacrylate, n-dodecyl methacrylate, n-tetradecyl methacrylate, n-hexadecyl methacrylate, 2-ethylhexyl methacrylate, allyl methacrylate, oleyl methacrylate, 2-propynyl methacrylate, 2-(dimethylamino)ethyl methacrylate, 2-(diethylamino)ethyl methacrylate, 2-(diisopropylamino)ethyl methacrylate, N-(2-aminoethyl) methacrylamide hydrochloride, 2-aminoethyl methacrylate hydrochloride, N-(3-aminopropyl)methacrylamide hydrochloride, 2-(tert-butylamino)ethyl methacrylate and the like. The above monomers may be employed separately or in various mixtures according to this invention.

The use of multifunctional acrylate and methacrylate will lead to the formation of cross-linked network polymers upon polymerization. Such polymers have desirable properties such as good mechanical strength, elasticity, toughness, and flexibility. Examples of multifunctional acrylates and methacrylates of use in this invention include, but are not limited to, ethylene glycol dimethacrylate (EGDMA), trimethylolpropane trimethacrylate, trimethyloyl triacrylate, pentaerythritol triacrylate, pentaerythritol tetraacrylate, bisphenol A dimethacrylate, di(trimethylolpropane) tetraacrylate (DTTA), 1-(acryloyloxy)-3-(methacryloyloxy)-2-propanol (AOMOP), trimethylolpropane ethoxylate triacrylate (TPETA), dipentaerythritol pentaacrylate, hexane diacrylate, poly(ethylene glycol) dimethacrylate (PEGDMA), and 1,6-hexandiol dimethacrylate (HDDMA), 1,4-butandiol dimethacrylate, 1,3-butandiol dimethacrylate, 1,6-hexandiol diacrylate, 1,4-butandiol diacrylate, 1,3-butandiol diacrylate. Preferably, this invention includes the use of multifunctional acrylates or methacrylate compounds such as EGDMA, PEGDMA, and HDDMA alone or in combination with one or more monofunctional acrylates or methacrylates.

Preferably, the acrylic or methacrylic acid, or ester thereof, makes up less than 25% by mass, preferably 5 to 20% by mass, or more preferably 10 to 15% by mass of the oil phase used in preparing the hydrogel capsule of this invention.

The hydrogel capsule of this invention is produce by (a) providing an aqueous phase, which contains an emulsifier; (b) providing an oil phase, which contains at least one acrylic or methacrylic acid, or ester thereof, and a fragrance or odorant; (c) emulsifying the aqueous phase of (a) with the oil phase of (b) to produce an emulsion; (d) polymerizing the emulsion to produce a hydrogel capsule with a fragrance or odorant encapsulated therein; and (e) curing the hydrogel capsule.

The aqueous phase of the method includes an emulsifier and water. As is conventional in the art, an emulsifier is an agent used to bind together normally noncombinative substances, such as oil and water. It can be anionic, cationic or nonionic in nature. Examples of suitable emulsifiers include, but are not limited to, polyvinyl alcohol, e.g., a partially or completely hydrolyzed polyvinyl acetate (Biehn & Ernsberger (1948) *Ind. Eng. Chem.* 40:1449-1453), d-α-tocopheryl polyethylene glycol 1000 succinate (Mu & Feng (2003) *Pharma. Res.* 20:1864-1872), PLURACARE or poloxamer, or polyvinyl pyrrolidone. The PLURACARE block copolymers are synthetic copolymers of propylene oxide and ethylene oxide. In certain embodiments, the emulsifier is a hydrolyzed polyvinyl acetate such as a MOWIOL emulsifier manufactured by Hoechst A.G. (Frankfurt, Germany).

The oil phase of the method of this invention includes at least one acrylic or methacrylic acid, or ester thereof, as described above; a fragrance or odorant as described above; and an oil. Exemplary oils of use herein include ISOPAR M (an isoparaffinic fluid) and the other ISOPAR variants available from ExxonMobile Corp.; caprylic and capric triglycerides (e.g., NEOBEE M-5, NEOBEE M-20, triglycerides of coconut oil; and NEOBEE 895, caprylic triglyceride, available from Stepan Chemicals), light mineral oils, light mineral waxes, vegetable oils, light vegetable waxes, diethylphthalate, butylbenzoate, benzylbenzoate, ester solvents, triacetin, and glycol-based water-insoluble solvents.

Once the oil phase and aqueous phase are combined, the mixture is emulsified according to known techniques, e.g., homogenization, shaking, or exposure to ultrasound. Subsequently, the acrylic or methacrylic acid, or ester thereof, is polymerized to produce a hydrogel capsule with a fragrance or odorant encapsulated therein. Polymerization can be carried out using known methods of free radical polymerization. These include the use of initiators such as ammonium persulfate and azobis(isobutyronitrile) (AIBN) and catalysts such as sodium metabisulfate or tetramethylethylenediamine. Polymerization can be carried out at room temperature (e.g., 20-25° C.) for one to several hours. The initiators and catalyst can be added in one-step, or intermittently, or in multiple steps.

The resulting hydrogel capsules are subsequently cured, first at room temperature (c.a. 20° C.) then cure at an elevated temperature of at least 40° C. In certain embodiments, the hydrogel capsules are cured at temperature in the range of 55 and 65° C.

Hydrogel capsules of this invention can also be additionally coated with a polymeric material, i.e., a deposition aid. The coating polymer can be anionic, cationic or nonionic. The polymeric coating can be added during the preparation of the capsules or after the capsules are made. These polymers include, but not limited to MERQUAT 100 Polymer (Polyquaternium-6; Lubrizol, Cleveland, Ohio), LUPAMIN 9095 (polyvinylamine; BASF, Mount Olive, N.J.), ZEMAC E400 (Vertellus, Zeeland, Mich.), TICA-ALGIN HG 600 F (Sodium alginate; TIC Gums, White Marsh, Md.), Chitosan (Sigma-Aldrich), Tannic acid (Graham Chemical, Barrington, Ill.). The polymer may be added after the capsules are formed or in the process.

Hydrogel capsules of this invention have a mean diameter in the range of 1 to 100 µm, more preferably in the range of 1 to 20 µm, most preferably in the range of 5 to 10 µm; and are stable during storage.

The hydrogel capsules of this invention are also suitable for laundry care, personal care, therapeutic, cosmetic or cosmeceutic products. In particular, the hydrogel capsules of this invention are of particular use in wash-off products, which are understood to be those products that are applied for a given period of time and then are removed. Such products include laundry care products such as rinse conditioners, liquid detergent, powder detergent, and fabric refresher; as well as personal care products such as hair shampoos, hair conditioners, hair rinses, antiperspirant/deodorant, hand sanitizer, bar soaps, and body washes and the like. These products are well known in the art. For example, fabric softener systems are described in U.S. Pat. No. 6,335,315, U.S. Pat. No. 5,674,832, U.S. Pat. No. 5,759,990, U.S. Pat. No. 5,877,145, U.S. Pat. No. 5,574,179; U.S. Pat. No. 5,562,849, U.S. Pat. No. 5,545,350, U.S. Pat. No. 5,545,340, U.S. Pat. No. 5,411,671, U.S. Pat. No. 5,403,499, U.S. Pat. No. 5,288,417, U.S. Pat. No. 4,767,547, and U.S. Pat. No. 4,424,134. Liquid dish detergents are described in U.S. Pat. No. 6,069,122 and U.S. Pat. No. 5,990,065; automatic dish detergent products are described in U.S. Pat. No. 6,020,294, U.S. Pat. No. 6,017,871, U.S. Pat. No. 5,968,881, U.S. Pat. No. 5,962,386, U.S. Pat. No. 5,939,373, U.S. Pat. No. 5,914,307, U.S. Pat. No. 5,902,781, U.S. Pat. No. 5,705,464, U.S. Pat. No. 5,703,034, U.S. Pat. No. 5,703,030, U.S. Pat. No. 5,679,630, U.S. Pat. No. 5,597,936, U.S. Pat. No. 5,581,005, U.S. Pat. No. 5,559,261, U.S. Pat. No. 4,515,705, U.S. Pat. No. 5,169,552, and U.S. Pat. No. 4,714,562. Liquid laundry detergents which can use the present invention include those systems described in U.S. Pat. No. 5,929,022, U.S. Pat. No. 5,916,862, U.S. Pat. No. 5,731,278, U.S. Pat. No. 5,565,145, U.S. Pat. No. 5,470,507, U.S. Pat. No. 5,466,802, U.S. Pat. No. 5,460,752, U.S. Pat. No. 5,458,810, U.S. Pat. No. 5,458,809, U.S. Pat. No. 5,288,431, U.S. Pat. No. 5,194,639, U.S. Pat. No. 4,968,451, U.S. Pat. No. 4,597,898, U.S. Pat. No. 4,561,998, U.S. Pat. No. 4,550,862, U.S. Pat. No. 4,537,707, U.S. Pat. No. 4,537,706, U.S. Pat. No. 4,515,705, U.S. Pat. No. 4,446,042, and U.S. Pat. No. 4,318,818. Shampoo and conditioners that can employ the present invention include those described in U.S. Pat. No. 6,162,423, U.S. Pat. No. 5,968,286, U.S. Pat. No. 5,935,561, U.S. Pat. No. 5,932,203, U.S. Pat. No. 5,837,661, U.S. Pat. No. 5,776,443, U.S. Pat. No. 5,756,436, U.S. Pat. No. 5,661,118, U.S. Pat. No. 5,618,523, U.S. Pat. No. 5,275,755, U.S. Pat. No. 5,085,857, U.S. Pat. No. 4,673,568, U.S. Pat. No. 4,387,090 and U.S. Pat. No. 4,705,681.

Personal care products, including cosmetic, cosmeceutic or pharmaceutical preparations can be formulated as "water-in-oil" (W/O) type emulsions, "oil-in-water" (O/W) type emulsions or as multiple emulsions, for example of the water-in-oil-in-water (W/O/W) type, as a PIT emulsion, a Pickering emulsion, a micro-emulsion or nano-emulsion. Emulsions that are particularly preferred are of the "oil-in-water" (O/W) type or water-in-oil-in-water (W/O/W) type.

In certain embodiments, the final composition or product may be in the form of an oil, a gel, a roll-on, a solid stick, a lotion, a cream, a milk, an aerosol, a spray, a powder, a foam, a shampoo, a hair conditioner, a lacquer or a make-up.

The invention is described in greater detail by the following non-limiting examples.

Example 1

Preparation of Hydrogel Capsules with Post-Curing in Oven

Emulsifier, 10 wt. % MOWIOL 3-83 (Kuraray America Inc.), was prepared in aqueous solution by dissolving MOWIOL 3-83 powder in deionized (DI) water under stirring at 60° C. for 3 hours. The 10% MOWIOL 3-83 (M-3-83) solution was used as a stock solution.

Fragrance emulsion was formed by adding 20 gram of 10% M-3-83 solution into 80 grams of DI water to form the water phase, which was deoxygenated by bubbling $N_2$ for 30 minutes. In a separate container, ten gram of ethylene glycol dimethacrylate (EGDMA, Aldrich) was added into a fragrance oil mixture containing 64 grams of Posh Special (IFF, Union Beach, N.J.) and 16 grams of NEOBEE medium chain triglycerides (as hydrophobe) to form the oil phase. The oil phase was purged with $N_2$ for 30 minutes. The aqueous phase and the oil phase were then combined and homogenized at 9500 rpm for 3 minutes to form the emulsion.

Fragrance capsules were formed by placing the emulsion in a 16 ounce jar and purging the emulsion with $N_2$ for 10 minutes. Five grams of a water solution containing 0.3 g ammonium persulfate (APS, Sigma-Aldrich) as the initiator was added to the emulsion. After another 15 minutes, 5 grams of catalyst solution containing 0.4 gram sodium metabisulfate (Sigma-Aldrich) was added to the emulsion to start polymerization. The emulsion was kept at room temperature (~20° C.) for three and half hours and was then transferred to an oven at 65° C. The fragrance capsules were allowed to cure at 65° C. overnight. Alternatively, the slurry can be cured for the desired amount of time using a temperature-controlled water or oil bath.

Example 2

Preparation of Hydrogel Capsule with Ethylene Glycol Dimethacrylate (EGDMA)/Methyl Methacrylate (MMA)

Fragrance emulsion was formed by adding 20 grams of 10% M-3-83 solution into 80 grams of DI water to form the aqueous phase, which was deoxygenated by bubbling $N_2$ for 30 minutes. In a separate container, 8 grams ethylene glycol dimethacrylate (EGDMA, Aldrich) and 2 grams methyl methacrylate (MMA) were added into a fragrance oil mixture containing 64 grams Posh Special (IFF, Union Beach, N.J.) and 16 grams NEOBEE medium chain triglycerides to form the oil phase. The oil phase was purged with $N_2$ for 30 minutes. The aqueous phase and the oil phase were then combined and homogenized at 9500 rpm for 3 minutes to form the emulsion.

Fragrance capsules were formed by placing the emulsion in a 16 ounce jar and purging the emulsion with $N_2$ for 10 minutes. Five gram of a water solution containing 0.3 gram ammonium persulfate (APS, Sigma-Aldrich) as the initiator was added into the emulsion. After another 15 minutes, 5 grams of catalyst solution containing 0.4 gram sodium metabisulfate (Sigma-Aldrich) was added to the emulsion to start polymerization. The emulsion was kept at room temperature (~20° C.) for three and half hours and then transferred to an oven at 65° C. The capsules were allowed to cure at 65° C. overnight. Alternatively, the slurry can be cured for the desired amount of time using a temperature-controlled water or oil bath.

Example 3

Preparation and Characterization of Hydrogel Capsule with Poly(Ethylene Glycol) Dimethacrylate A fragrance emulsion was prepared by adding twenty grams of 10% M-3-83 solution to 80 grams DI water to form the aqueous phase, which was deoxygenated by bubbling $N_2$ for minutes. In a separate container, ten grams of poly (ethylene glycol) dimethacrylate (PEGDMA, $M_w$=595, Sigma-Aldrich) was then added to a fragrance oil mixture containing 64 grams Posh Special (IFF, Union Beach, N.J.) and 16 grams NEOBEE medium chain triglycerides to form the oil phase. The oil phase was purged with $N_2$ for 30 minutes. The aqueous phase and the oil phase were then combined and homogenized at 9500 rpm for 3 minutes to form the emulsion.

Fragrance capsules were formed placing the emulsion in a 16 ounce jar and purging the emulsion with $N_2$ inside for 10 minutes. Five grams of a water solution containing 0.3 gram ammonium persulfate (APS, Sigma-Aldrich) as the initiator was added to the emulsion. After another 15 minutes, 5 grams catalyst solution containing 0.4 gram sodium metabisulfate (Sigma-Aldrich) was added to the emulsion to start polymerization. The emulsion was kept at room temperature (~20° C.) for three and half hours and then transferred into an oven at 65° C. The hydrogel capsules were allowed to cure overnight at 65° C. Alternatively, the slurry can be cured for the desired amount of time using a temperature-controlled water or oil bath.

Example 4

Preparation of Hydrogel Capsule with Different Post-Curing Temperatures

Fragrance emulsion was prepared by adding 40 grams of 10% M-3-83 solution to 160 grams DI water to form the aqueous phase, which was deoxygenated by bubbling $N_2$ for 30 minutes. In a separate container, twenty gram of EGDMA was added into a fragrance oil mixture containing 128 grams Posh Special (IFF, Union Beach, N.J.) and 32 grams NEOBEE medium chain triglycerides to form the oil phase. The oil phase was purged with $N_2$ for 30 minutes. The aqueous phase and the oil phase were then combined and homogenized at 9500 rpm for 3 minutes to form the emulsion.

Fragrance capsules were formed by placing the emulsion in a 32 ounce jar and purging the emulsion with $N_2$ for 10 minutes. Subsequently, 10 grams water solution containing 0.6 gram initiator ammonium persulfate (APS, Sigma-Aldrich) was added to the emulsion. After another 15 minutes, 10 grams catalyst solution containing 0.8 gram sodium metabisulfate was added to the emulsion to start polymerization at room temperature (~20° C.) and hydrogel capsules were allowed to form for three and a half hours. The curing temperature was then varied from 40° C. to 65° C. with 5° C. increments. The capsule slurry was kept at the individual curing temperatures for 3 hours.

Example 5

Preparation of Hydrogel Capsule with Varying Post-Curing Times

Fragrance emulsion was prepared by adding 40 grams of 10% M-3-83 solution to 160 grams DI water to form the aqueous phase, which was deoxygenated by bubbling $N_2$ for 30 minutes. In a separate container, twenty gram of EGDMA was added into a fragrance oil mixture containing 128 grams Posh Special (IFF, Union Beach, N.J.) and 32 grams NEOBEE medium chain triglycerides to form the oil phase. The oil phase was purged with $N_2$ for 30 minutes. The aqueous phase and the oil phase were then combined and homogenized at 9500 rpm for 3 minutes to form the emulsion.

Fragrance capsules were formed by placing the emulsion in a 32 ounce jar and bubbling $N_2$ into the emulsion for 10 minutes. To the emulsion was then added 10 grams water solution containing 0.6 gram initiator ammonium persulfate (APS, Sigma-Aldrich). After another 15 minutes, grams catalyst solution containing 0.8 gram sodium metabisulfate was added into the emulsion to start polymerization at room temperature for three and half hours (~20° C.) to form hydrogel capsule. The curing temperature was then varied from 40° C. to 65° C. with 5° C. increments. The capsule slurry was kept at the individual curing temperature for different periods of curing length.

Example 6

Preparation of Hydrogel Capsule with Shorter Polymerization Time in Room Temperature Fragrance emulsion was formed by adding 40 grams of 10% M-3-83 solution to 160 grams DI water to form the aqueous phase, which was deoxygenated by bubbling $N_2$ for 30 minutes. In a separate container, 20 gram of EGDMA was added into a fragrance oil mixture containing 128 grams Posh Special (IFF, Union Beach, N.J.) and 32 grams NEOBEE medium chain triglycerides to form the oil phase. The oil phase was purged with $N_2$ for 30 minutes. The aqueous phase and the oil phase were then combined and homogenized at 9500 rpm for 3 minutes to form the emulsion.

Fragrance capsules were prepared by placing the emulsion in a 32 ounce jar and purging the emulsion with $N_2$ for 10 minutes. Subsequently, 10 grams of water solution, containing 0.6 gram initiator ammonium persulfate (APS, Sigma-Aldrich), was added to the emulsion. After another 15 minutes, 10 grams catalyst solution containing 0.8 gram sodium metabisulfate was added to the emulsion to start polymerization at room temperature for two and half hours (~0.20° C.) to form hydrogel capsule. The curing temperature was then increased to 60° C. and cured for 3 hours.

Example 7

Preparation of Hydrogel Capsule Loading with Fragrance Psychedelic Gourmand Fragrance emulsion was prepared by adding 40 grams of 10% M-3-83 solution to 160 grams DI water to form the aqueous phase, which was deoxygenated by bubbling $N_2$ for 30 minutes. In a separate container, 20 grams of EGDMA was added into a fragrance oil mixture containing 128 grams Posh Special (IFF, Union Beach, N.J.) and 32 grams NEOBEE medium chain triglycerides to form the oil phase. The oil phase was purged with $N_2$ for 30 minutes. The aqueous phase and the oil phase were then combined and homogenized at 9500 rpm for 3 minutes to form the emulsion.

Fragrance capsules were prepared by placing the emulsion in a 32 ounce jar and purging the emulsion with $N_2$ for 10 minutes. Subsequently, 10 grams of water solution, containing 0.6 gram initiator ammonium persulfate (APS, Sigma-Aldrich) was added to the emulsion. After another 15 minutes, 10 grams catalyst solution containing 0.8 gram sodium metabisulfate was added into the emulsion to start polymerization at room temperature for three and half hours (~20° C.) to form hydrogel capsule. The curing temperature was then increased to 55° C. and cured for 3 hours.

Example 8

Preparation of Hydrogel Capsule Loading with Fragrances Apple, Greenfield, and Perfect Match Procedures in Example 7 were repeated for preparation of fragrance capsules loaded with either Apple, Greenfield, or Perfect Match.

Example 9

Preparation of Hydrogel Capsule with Different Wall Materials

Fragrance emulsion was prepared by adding 40 grams of 10% M-3-83 solution to 160 grams DI water to form the aqueous phase which was deoxygenated by bubbling $N_2$ for 30 minutes. In a separate container, 20 grams of 1,6 hexandiol dimethacrylate (HDDMA, Aldrich) was added into a fragrance oil mixture containing 128 grams Posh Special (IFF, Union Beach, N.J.) and 32 grams NEOBEE medium chain triglycerides to form the oil phase. The oil phase was purged with $N_2$ for 30 minutes. The aqueous phase and the oil phase were then combined and homogenized at 9500 rpm for 3 minutes to form the emulsion.

Fragrance capsules were prepared by placing the emulsion in a 32 ounce jar and purging the emulsion with $N_2$ for 10 minutes. Subsequently, 10 grams water solution containing 0.6 gram initiator ammonium persulfate (APS, Sigma-Aldrich) was added to the emulsion. After another 15 minutes, 10 grams catalyst solution containing 0.8 gram sodium metabisulfate ($Na_2S_2O_5$, Sigma-Aldrich) was added to the emulsion to start polymerization at room temperature (~20° C.) and hydrogel capsules were formed for three and half hours. The capsule slurry was cured at 55° C. under stirring for three hours.

Example 10

Preparation of Hydrogel Capsules with 2-Step Addition of Initiator and Catalyst Fragrance emulsion was formed by adding 20 gram of 10% M-3-83 solution into 80 grams of DI water to form the water phase, which was deoxygenated by bubbling $N_2$ for 30 minutes. In a separate container, ten grams of ethylene glycol dimethacrylate (EGDMA, Aldrich) was added into a fragrance oil mixture containing 64 grams of Posh Special (IFF, Union Beach, N.J.) and 16 grams of NEOBEE medium chain triglycerides (as hydrophobe) to form the oil phase. The oil phase was purged with $N_2$ for 30 minutes. The aqueous phase and the oil phase were then combined and homogenized at 9500 rpm for 3 minutes to form the emulsion.

Fragrance capsules were formed by placing the emulsion in a 16-ounce jar and purging the emulsion with $N_2$ for 10 minutes. Two and a half grams of a water solution containing 0.1 gram ammonium persulfate (APS, Sigma-Aldrich) as the initiator was added to the emulsion. After another 15 minutes, 2.5 grams of catalyst solution containing 0.2 gram sodium metabisulfate (Sigma-Aldrich) was added to the emulsion to start polymerization. The emulsion was kept at room temperature (~20° C.) for three and half hours and was then transferred to a water bath at 55° C. After being cured at 55° C. for 0.5 hours, 2.5 grams of two solutions containing 0.1 gram ammonium persulfate and 0.2 gram sodium metabisulfate were added to the emulsion. The fragrance capsules were allowed to cure at 55° C. for another 3 hours.

Example 11

Preparation of Hydrogel Capsules with Intermittent-Step Addition of Initiator and Catalyst Fragrance emulsion was formed by adding 20 gram of 10% M-3-83 solution into 80 grams of DI water to form the water phase, which was deoxygenated by bubbling $N_2$ for 30 minutes. In a separate container, ten grams of ethylene glycol dimethacrylate (EGDMA, Aldrich) was added into a fragrance oil mixture containing 64 grams of Posh Special (IFF, Union Beach, N.J.) and 16 grams of NEOBEE medium chain triglycerides (as hydrophobe) to form the oil phase. The oil phase was purged with $N_2$ for 30 minutes. The aqueous phase and the oil phase were then combined and homogenized at 9500 rpm for 3 minutes to form the emulsion.

Fragrance capsules were formed by placing the emulsion in a 16-ounce jar and purging the emulsion with $N_2$ for 10 minutes. Two and a half grams of a water solution containing 0.1 gram ammonium persulfate (APS, Sigma-Aldrich) as the initiator was added to the emulsion. After another 15 minutes, 2.5 grams of catalyst solution containing 0.2 gram sodium metabisulfate (Sigma-Aldrich) was added to the emulsion to start polymerization. The emulsion was kept at room temperature (~20° C.) for three and half hours and was then transferred to water bath at 55° C. After being cured at 55° C. for 0.5 hours, 2.5 grams of two solutions containing 0.1 gram ammonium persulfate and 0.2 gram sodium metabisulfate were added to the emulsion drop-wise at 65° C. within a period of 2 hours. The fragrance capsules were allowed to cure at 55° C. for another 3 hours.

Example 12

Preparation of Hydrogel Capsules with Different Dispersant

Emulsifier, 10 wt. % PLUROCARE F127 or F68 Prill Surfactant (BASF Corporation), was prepared in aqueous solution by dissolving PLUROCARE F127 or F68 Prill Surfactant powder in DI water under stirring at 60° C. for 3 hours. The 10% PLUROCARE F127 or F68 Prill Surfactant solution was used as a stock solution.

Fragrance emulsion was formed by adding 20 grams of 10% PLUROCARE F127 or F68 Prill Surfactant solution into 80 grams of DI water to form the water phase, which was deoxygenated by bubbling $N_2$ for 30 minutes. In a separate container, ten grams of ethylene glycol dimethacrylate (EGDMA, Aldrich) was added into a fragrance oil mixture containing 64 grams of Posh Special (IFF, Union Beach, N.J.) and 16 grams of NEOBEE medium chain triglycerides (as hydrophobe) to form the oil phase. The oil phase was purged with $N_2$ for 30 minutes. The aqueous phase and the oil phase were then combined and homogenized at 9500 rpm for 3 minutes to form the emulsion.

Fragrance capsules were formed by placing the emulsion in a 16-ounce jar and purging the emulsion with $N_2$ for 10 minutes. Five grams of a water solution containing 0.3 gram ammonium persulfate (APS, Sigma-Aldrich) as the initiator was added to the emulsion. After another 15 minutes, 5 grams of catalyst solution containing 0.4 gram sodium metabisulfate (Sigma-Aldrich) was added to the emulsion to start polymerization. The emulsion was kept at room temperature (~20° C.) for three and half hours and was then transferred to a water bath at 55° C. The fragrance capsules were allowed to cure at 55° C. for three more hours.

Example 13

Preparation of Post-Addition CMC coating Hydrogel Capsules

Fragrance emulsion was formed by adding 20 grams of 10% M-3-83 solution into 80 grams of DI water to form the water phase, which was deoxygenated by bubbling $N_2$ for 30 minutes. In a separate container, ten grams of ethylene glycol dimethacrylate (EGDMA, Aldrich) was added into a fragrance oil mixture containing 64 grams of Posh Special (IFF, Union Beach, N.J.) and 16 grams of NEOBEE medium chain triglycerides (as hydrophobe) to form the oil phase. The oil phase was purged with $N_2$ for 30 minutes. The aqueous phase and the oil phase were then combined and homogenized at 9500 rpm for 3 minutes to form the emulsion.

Fragrance capsules were formed by placing the emulsion in a 16-ounce jar and purging the emulsion with $N_2$ for 10 minutes. Five grams of a water solution containing 0.3 gram ammonium persulfate (APS, Sigma-Aldrich) as the initiator was added to the emulsion. After another 15 minutes, 5 grams of catalyst solution containing 0.4 gram sodium metabisulfate (Sigma-Aldrich) was added to the emulsion to start polymerization. The emulsion was kept at room temperature (~20° C.) for three and half hours and was then transferred to a water bath at 55° C. The fragrance capsules were allowed to cure at 55° C. again.

After curing, the capsule slurry was allowed to cool down to room temperature. One hundred-twenty grams of 1% wt carboxymethyl cellulose (CMC, MW=250 kDa) aqueous solution was mixed into the hydrogel capsule slurry. The mixture was then transferred to a water bath at 55° C. The CMC-coated capsules were allowed to cure at 55° C. again.

Hydrogel capsules coated with other polymers can be prepared in a similar fashion. These polymers include, but not limited to MERQUAT 100 Polymer (Polyquaternium-6; Lubrizol, Cleveland, Ohio), LUPAMIN 9095 (polyvinylamine; BASF, Mount Olive, N.J.), ZEMAC E400 (Vertellus, Zeeland, Mich.), TICA-ALGIN HG 600 F (Sodium alginate; TIC Gums, White Marsh, Md.), Chitosan (Sigma-Aldrich), Tannic acid (Graham Chemical, Barrington, Ill.).

Example 14

Physical Characterization of Hydrogel Capsules

The hydrogel capsules were characterized by microscopic techniques. This also allowed an assessment of the mechanical strength of the dried hydrogel capsules. SEM analysis clearly demonstrated that the hydrogel capsule retained its physical integrity under stress.

Example 15

Particle Size Distribution of Hydrogel Capsules

This example illustrates the particle size distribution of hydrogel capsules as prepared in Example 4. The result from light scattering is shown in FIG. 1. The average size of hydrogel capsules was about 8.7 µm.

Example 16

Storage Stability Evaluation of Hydrogel Capsules

To evaluate the storage stability of the hydrogel capsules, the capsules prepared in Example 4 were dispersed in a customer shampoo base, Magic Botanicals (MB), at 1%. The samples were then aged at 55° C. for a period of 3 days and the amount of fragrance leached out was measured by gas chromatography direct injection. The results of this analysis are presented in Table 2.

TABLE 2

| Sample | Fresh | 3 days at 55° C. |
|---|---|---|
| Sample 1 | <10% | 23% |
| Sample 2 | <10% | 27% |

This analysis indicated that the capsules retained the majority of the fragrance after 3 days at 55° C., demonstrating their robust storage stability.

Example 17

Encapsulation Performance of Hydrogel Capsules

Using the sample prepared in Example 4, a 0.2% dispersion of the capsule was prepared by diluting 0.2 gram of the slurry with 100 gram of DI water. One gram of the diluted capsule slurry was directly applied to each side of a 4×6 fabric swatch. The swatches were air-dried overnight and the headspace of the fabrics was analyzed before and after stirring with stainless steel ball bearings to break intact capsules. The results of this analysis are presented in Table 3.

TABLE 3

|  | Unstirred | Stirred |
|---|---|---|
| Headspace | 57642 | 409601 |
| Ratio Stirred/Unstirred | — | 7.1 |

The results clearly showed that there was a significant increase in headspace after the capsules were disrupted. This example demonstrates that the capsules can re lease their contents after mechanical perturbation and produce significant consumer benefits.

Example 18

Demonstration of the Perfumery Performance of Hydrogel Capsules in Fabric Refresher Application To establish the consumer benefits of the hydrogel capsules, the capsule slurry prepared in Example 4 was blended into a fabric refresher base and evaluated for its consumer benefits. The fragrance load was 0.5% neat equivalent. For comparison, a similar solution was prepared using neat fragrance at 0.5%. Fabric towels were sprayed with the dispersion and were air-dried overnight before being evaluated by panel of 12 judges. The fragrance intensity was rated from a Labeled Magnitude Scale ranging from 0 to 50. A numerical value of 5 indicates the fabric only produces a very weak intensity while a value of 30 indicates the fabric generates a strong smell. The results of this analysis are presented in Table 4.

TABLE 4

| Samples | Pre-rubbing intensity | Post-rubbing intensity | $I_{post, capsule}/I_{post, neat}$ |
|---|---|---|---|
| Neat | 8.2 | 8.2 |  |
| Hydrogel capsule after 5 hours | 6.7 | 15.0 | 2.2 |
| Hydrogel capsule after 24 hours | 9.1 | 19.2 | 2.1 |

This analysis indicated that the hydrogel capsule provided significant and long-lasting perfumery benefits.

Example 19

Demonstration of the Perfumery Performance of Hydrogel Capsules in a Laundry Application To establish the performance of the hydrogel capsules in laundry applications, the capsule slurry prepared by the current invention was blended into a model rinse conditioner solution that contained 24% cationic surfactant. The fragrance load was 0.5% neat equivalent. For comparison, a similar solution was prepared using neat fragrance at 0.5%. The perfumery benefit of the capsules was evaluated by conducting a laundry experiment using accepted experimental protocols using a US washing machine. Terry towels were used for the washing experiments and were air-dried overnight before being evaluated by panel of 12 judges. The fragrance intensity was rated from a LMS scale ranging from 0 to 30. A numerical value of 5 would suggest the fabric only produced very week intensity while a value of 30 indicated the laundered towel generated a strong smell. The results are presented in Table 5.

TABLE 5

| Samples | Pre-rubbing intensity | Post-rubbing intensity | $I_{pre, capsule}/I_{pre, neat}$ | $I_{post, capsule}/I_{post, neat}$ |
|---|---|---|---|---|
| Neat | 2.5 | 3.0 |  |  |
| Hydrogel capsule | 3.5 | 13.5 | 1.4 | 4.5 |

It was quite apparent that the hydrogel fragrance capsules produced much greater fragrance intensity at the pre-rubbing and post-rubbing stages. However, the increase in fragrance intensity was much more pronounced in the post-rubbing stage. This demonstrated that the hydrogel fragrance capsules prepared with the current invention were able to retain the fragrance effectively and were capable of delivering the full consumer benefits of the fragrance products.

Example 20

Figure 2:
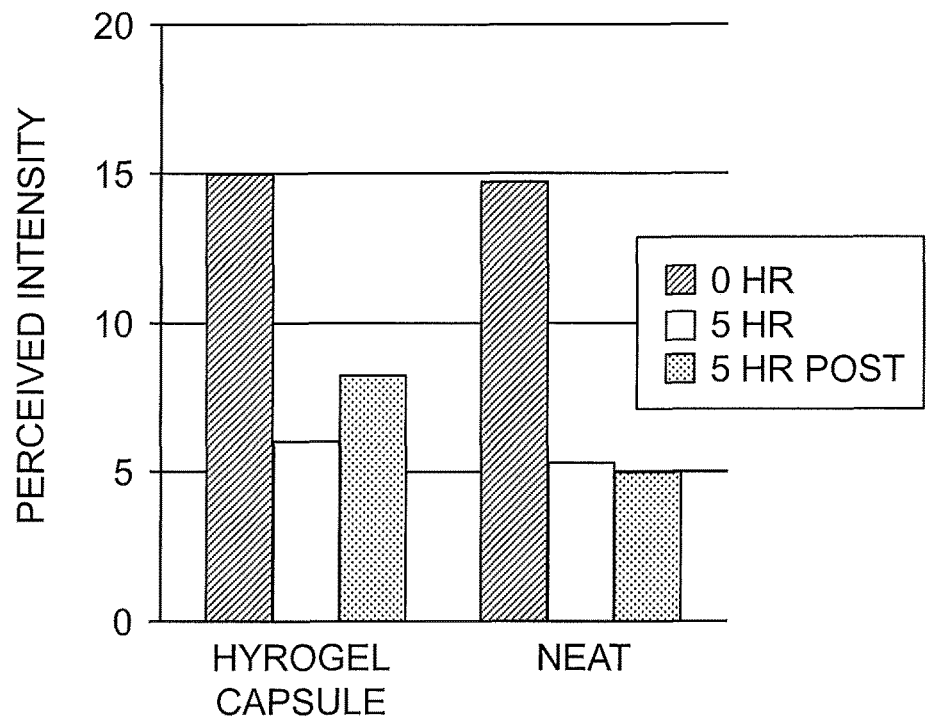
FIG. 2 shows hand sanitizer sensory performance of hydrogen capsules. n=16.

Demonstration of the Application Benefit of Hydrogel Capsule in Hand Sanitizer Application Application benefit of the hydrogel capsule in a personal care product was evaluated using a hand sanitizer formulation. To conduct the experiments, the capsule slurry was dispersed in a hand sanitizer base at 0.5% neat fragrance equivalent. The hand sanitizer base contained 62% ethanol. The sensory performance is shown in FIG. 2. The example clearly demonstrated that the product containing hydrogel capsules had much stronger perfumery intensity than the market product. Thus, the hydrogel capsule may deliver excellent consumer benefits both in the pre- and post-rubbing stage.

Example 21

Figure 3:
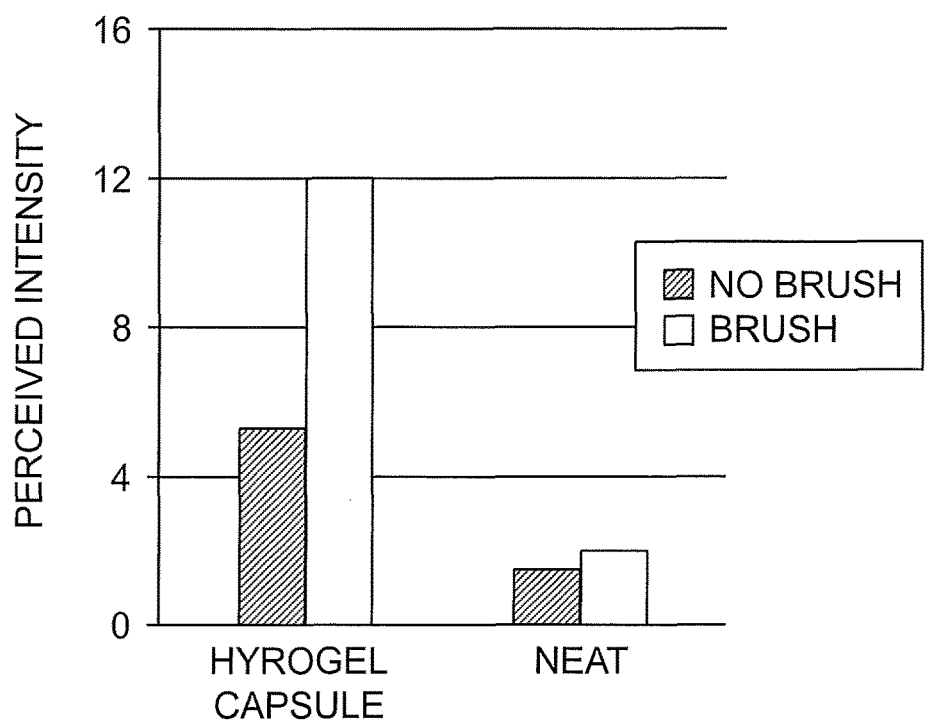
FIG. 3 shows the sensory performance of hydrogen capsules in a hair conditioner formulation.

Demonstration of the Application Benefit of Hydrogel Capsule in Hair Conditioner Application Application benefit of the hydrogel capsule in a personal care product was further evaluated using a hair conditioner formulation. The sensory performance is shown in FIG. 3. To conduct the experiments, the capsule slurry was dispersed in a hair conditioner base at 0.5% neat fragrance equivalent. The hair conditioner base was a magick botanicals oil-free conditioner base. To evaluate the benefit of hydrogel capsules, the capsule containing product was applied to a bundle of 4 hair strands which weighed about 40 grams and washing was done according the following protocols. Two bundles of hair (8 strands) were wet under water ($H_2O$ temperature, 100° F./38° C.; Flow rate, 1 gallon/minute) and lightly squeezed to remove excess water. The hair was placed onto a balance and 2 grams of unfragranced shampoo was applied directly onto the wet hair. The hair was lathered between the palms of two hands 10× clockwise and 10× counter-clockwise, keeping the wax part of the swatches between two fingers (not to spread wax over surface of hair). The hair swatches were allowed to stand for 15 seconds and subsequently rinsed under a stream of water for 45 seconds. The process was repeated with hair conditioner, with the excess gently squeezed out. The hair was hung to dry overnight. The dried samples were then evaluated by 16 trained panelists. The results are given in FIG. 3. The example clearly demonstrates that the product containing hydrogel capsules had much stronger perfumery intensity than the neat fragrance. Thus, the hydrogel capsule may deliver excellent consumer benefits both in the pre- and post-rubbing stage.

Example 22

Demonstration of the Application Benefit of Hydrogel Capsule in an AP/DEO (Antiperspirant Deodorant) Application The following example illustrates the application benefit of the capsules prepared by current invention in anti-perspirent (AP) roll-on base. A fragrance capsule slurry was prepared using the process described in Example 13. The capsule slurry was dispersed in an AP-roll base at 0.5% neat fragrance equivalent. The base typically contained 1 to 3% anionic surfactant, 10 to 20%, aluminium chlorohydrate, less than 1% silica, 1 to 2% *Helianthus annuus* and water.

The prepared product containing the capsule (100 µl) in AP roll-on based was applied to the forearm of six panelists and the fragrance intensity was evaluated immediately after application and five hours after application with rubbing by 20 trained intensity judges and data was analyzed statistically. The fragrance intensity was rated from a scale ranging from 0 to 30. A numerical value of 5 suggested the subject only produced very week intensity while a value of 30 indicated the subject generated a strong smell.

Figure 4:
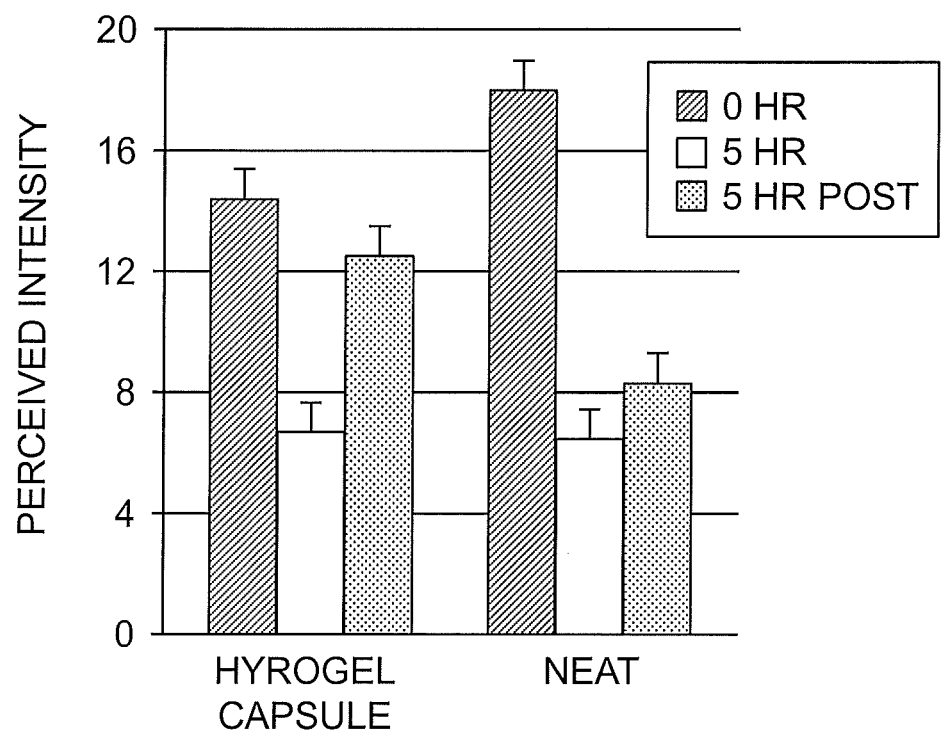
FIG. 4 shows the sensory performance of hydrogen capsules in an antiperspirant/deodorant roll-on formulation.

It was found that, after rubbing, the product containing capsule generated significantly greater intensity than a product containing neat fragrance only. The results are given in FIG. 4. This example clearly demonstrated that the product containing hydrogel capsules had much stronger perfumery intensity than the neat product after 5 hours. Thus, the hydrogel capsule may deliver excellent consumer benefits both in the pre- and post-rubbing stage.

Example 23

Deodorant and Antiperspirant

An exemplary wax-based deodorant is prepared by mixing paraffin wax (10-20%), hydrocarbon was (5-10%), white petrolatum (10-15%), acetylated lanolin alcohol (2-4%), diisopropyl adipate (4-8%), Mineral Oil (40-60%) and preservative (as needed); heating the mixture to 75° C. until melted, and, with stirring at 75° C., adding 4.0 parts by weight of an encapsulated fragrance of this invention.

An exemplary glycol/soap type deodorant is prepared by combining propylene glycol (60-70%), sodium stearate (5-10%), distilled water (20-30%) and 2,4,4-trichloro-2'-hydroxy diphenyl ether (0.01-0.5%); and heating the mixture, with stirring, to 75° C. until the sodium stearate has dissolved. The resulting mixture is cooled to 40° C. and encapsulated fragrance is added to the formulation.

An exemplary antiperspirant deodorant (soft solid) is prepared by combining cyclopentasiloxane (60%), dimethicone (10%), zirconium aluminum trichlorohydrex glycine (25%), encapsulated fragrance (2.5%) and fumed silica (2.5%).

Example 24

Body Wash

An exemplary body wash is composed of PLANTAPON 611 L (SLES, Cap Betaine, Lauryl Glycoside; 22%), ammonium lauryl sulfate (2.5%), LAMESOFT OP65 (Coco Glucoside, Glyceryl Oleate; 3%), polyquaternium 10-10 (0.5%), acrylates copolymer (0.5%), neat fragrance (0.3%), encapsulated fragrance (1%), DMDM hydantoin (0.3%), glycerin (3%) and water (q.s. 100%).

Example 25

Hair Products

An exemplary 2-in-1 hair shampoo is composed of sodium laureth sulfate (10%), cocamidopropyl betaine (7%), glyceryl stearate (2%), cetearyl alcohol (3%), panthenol (0.2%), acrylates copolymer (1.2%), dimethicone (1.5%), polyquaternium 10 (0.2%), encapsulated fragrance (1%), preservative (as needed), water (q.s. 100%), and NaOH to pH 6.0.

An exemplary hair gel is compose of PVP (3%), acrylates/C10-30 alkyl methacrylate copolymer (3%), denatured alcohol (10%), encapsulated fragrance (1%), Microcare PHG (0.5%), and water (q.s. 100%).

Example 26

Hand Sanitizer

An exemplary hand sanitizer is composed of acrylates C10-30 alkyl acrylate copolymer (0.2-0.5%), ethanol (60%), isopropanol (10%), glycerin (4%), encapsulated fragrance (1-5%), and water (q.s. 100%).

What is claimed is:

1. A hydrogel capsule comprising a fragrance or odorant encapsulated in one polymerized acrylic or methacrylic acid, or ester thereof, wherein the hydrogel capsule has a mean diameter in the range of 1 to 100 µm; the fragrance or odorant is encapsulated in the hydrogel capsule during polymerization of the one acrylic or methacrylic acid, or ester thereof contained in an oil phase; the oil phase by mass consists essentially of: (i) 60 to 90% of the fragrance or odorant, (ii) 10 to 15% of the one acrylic or methacrylic acid, or ester thereof, and (iii) an oil selected from the group consisting of an isoparaffinic fluid, a caprylic triglyceride, a capric triglyceride, a light mineral oil, a light mineral wax, a vegetable oil, a light vegetable wax, diethylphthalate, butylbenzoate, benzylbenzoate, an ester solvent, triacetin, and a glycol-based water-insoluble solvent and combinations thereof.

2. The hydrogel capsule of claim 1, wherein the hydrogel capsule has a mean diameter in the range of 1 to 20 μm.

3. The hydrogel capsule of claim 1, wherein the one acrylic or methacrylic acid, or ester thereof is a multifunctional acrylate or methacrylate.

4. The hydrogel capsule of claim 3, wherein the multifunctional acrylate or methacrylate is ethylene glycol diacrylate, ethylene glycol dimethacrylate, poly(ethylene glycol) dimethacrylate, or 1,6-hexandiol dimethacrylate.

5. The hydrogel capsule of claim 3, wherein the multifunctional acrylate or methacrylate is ethylene glycol dimethacrylate.

6. The hydrogel capsule of claim 3, wherein the capsules are additionally coated with another polymeric material.

7. The hydrogel capsule of claim 6, wherein the polymeric material is polyquaternium-6, polyvinylamine, sodium alginate, tannic acid, or a combination thereof.

8. A consumer product comprising the hydrogel capsule of claim 1.

9. The consumer product of claim 8, wherein said consumer product is a laundry care, personal care, therapeutic, cosmetic or cosmeceutic product.

10. The consumer product of claim 9, wherein the personal care product is a hair shampoo, hair conditioner, hair rinse, antiperspirant deodorant, hand sanitizer, bar soap or body wash.

11. The consumer product of claim 10, wherein the personal care product is formatted as a stick, roll-on or aerosol spray.

12. The consumer product of claim 9, wherein the laundry care product is a rinse conditioner, liquid detergent, powder detergent or fabric refresher.

13. A method for producing a hydrogel capsule with a fragrance or odorant encapsulated therein comprising
(a) providing a aqueous phase comprising an emulsifier;
(b) providing an oil phase consisting essentially of one acrylic or methacrylic acid, or ester thereof at a level of 10 to 15% by mass, 60% to 90% of a fragrance or odorant, and an oil selected from the group consisting of an isoparaffinic fluid, a caprylic triglyceride, a capric triglyceride, a light mineral oil, a light mineral wax, a vegetable oil, a light vegetable wax, diethylphthalate, butylbenzoate, benzylbenzoate, an ester solvent, triacetin, and a glycol-based water-insoluble solvent and combinations thereof;
(c) emulsifying the aqueous phase of (a) with the oil phase of (b) to produce an emulsion;
(d) polymerizing the emulsion to produce a hydrogel capsule with a fragrance or odorant encapsulated therein; and
(e) curing the hydrogel capsule.

14. The method of claim 13, wherein the one acrylic or methacrylic acid, or ester thereof is a multifunctional acrylate or methacrylate.

15. The method of claim 14, wherein the multifunctional acrylate or methacrylate is ethylene glycol diacrylate, ethylene glycol dimethacrylate, poly(ethylene glycol) dimethacrylate, or 1,6-hexandiol dimethacrylate.

16. The method of claim 14, wherein the multifunctional acrylate or methacrylate is ethylene glycol dimethacrylate.

17. The method of claim 13, wherein the hydrogel capsule is cured at a temperature of at least 40° C.

18. The method of claim 13, wherein the hydrogel capsule is cured at a temperature between 55 and 95° C.

19. The method of claim 13, wherein the hydrogel capsule is cured at a temperature between 55 and 65° C.

20. The method of claim 13, wherein the capsules are additionally coated with another polymeric material.

21. A hydrogel capsule comprising a fragrance or odorant encapsulated in one polymerized acrylic or methacrylic acid, or ester thereof, wherein the hydrogel capsule has a mean diameter in the range of 1 to 100 μm; the fragrance or odorant is encapsulated in the hydrogel capsule during polymerization of the one acrylic or methacrylic acid, or ester thereof contained in an oil phase; the oil phase by mass consists essentially of: (i) 60 to 90% of the fragrance or odorant and (ii) 10 to 15% of the one acrylic or methacrylic acid, or ester thereof.

22. The hydrogel capsule of claim 21, wherein the one acrylic or methacrylic acid, or ester thereof is a multifunctional acrylate or methacrylate.

23. The hydrogel capsule of claim 22, wherein the multifunctional acrylate or methacrylate is ethylene glycol diacrylate, ethylene glycol dimethacrylate, poly(ethylene glycol) dimethacrylate, or 1,6-hexandiol dimethacrylate.

24. The hydrogel capsule of claim 22, wherein the multifunctional acrylate or methacrylate is ethylene glycol dimethacrylate.

25. The hydrogel capsule of claim 21, wherein the capsules are additionally coated with another polymeric material.

26. A consumer product comprising the hydrogel capsule of claim 21.

27. The consumer product of claim 26, wherein said consumer product is a laundry care, personal care, therapeutic, cosmetic or cosmeceutic product.

* * * * *